(12) United States Patent
Iwamaru et al.

(10) Patent No.: US 8,263,348 B2
(45) Date of Patent: Sep. 11, 2012

(54) ABNORMAL PRION PROTEIN BINDER, AND METHOD FOR DETECTION OF ABNORMAL PRION PROTEIN

(75) Inventors: Yoshifumi Iwamaru, Ibaraki (JP); Tetsuya Kuhara, Kanagawa (JP)

(73) Assignee: Morinaga Milk Industry Co., Ltd., Tokyo (JP)

( * ) Notice: Subject to any disclaimer, the term of this patent is extended or adjusted under 35 U.S.C. 154(b) by 180 days.

(21) Appl. No.: 12/742,169

(22) PCT Filed: Nov. 20, 2008

(86) PCT No.: PCT/JP2008/003396
§ 371 (c)(1),
(2), (4) Date: May 10, 2010

(87) PCT Pub. No.: WO2009/066454
PCT Pub. Date: May 28, 2009

(65) Prior Publication Data
US 2010/0221745 A1 Sep. 2, 2010

(30) Foreign Application Priority Data

Nov. 20, 2007 (JP) .................................. 2007-300388

(51) Int. Cl.
*C07K 14/00* (2006.01)
(52) U.S. Cl. .......................... 435/7.1; 530/412; 436/501
(58) Field of Classification Search .......................... None
See application file for complete search history.

(56) References Cited

U.S. PATENT DOCUMENTS

| 2002/0137114 A1 | 9/2002 | Voelkel et al. |
| 2003/0096736 A1 | 5/2003 | Kruzel et al. |

FOREIGN PATENT DOCUMENTS

| JP | 10-267928 A | 10/1998 |
| JP | 11-32795 A | 2/1999 |
| JP | 2003-121448 A | 4/2003 |
| WO | 00/72874 A1 | 12/2000 |
| WO | 02/57793 A2 | 7/2002 |
| WO | 2005/070969 A1 | 8/2005 |

OTHER PUBLICATIONS

European Search Report dated Dec. 16, 2010, issued in corresponding European Patent Application No. 08853136.3.
Gupta, Ajay Kumar et al.; "Lactoferrin and ceruloplasmin derivatized superparamagnetic iron oxide nanoparticles for targeting cell surface receptors"; Biomaterials, Elsevier Science Publishers BV., Barking, GB, vol., 25, No. 15, Jul. 1, 2004, pp. 3029-3040.
Takase, Kenji; "Reactions of denatured proteins with other cellular components to form insoluble aggregates and protection by lactoferrin"; FEBS Letters, Elsevier, Amsterdam, NL, vol. 441, No. 2, Dec. 18, 1998, pp. 271-274.
Iwamaru, Yoshifumi et al.; "Lactoferrin induces cell surface retention of prion protein and inhibits prion accumulation"; Journal of Neurochemistry, vol. 49, No. 20, Oct. 2006, pp. 6057-6064.
Negredo, Carmen et al.; "A novel real-time ultrasonic method for prion protein detection using plasminogen as a capture molecule"; Biomed Central Ltd. London, GB, vol. 7, No. 1, Jul. 20, 2007, pp. 1-7.
Soldi, Gemma et al.; "Stabilization of a Native Protein Mediated by Ligand Binding Inhibits Amyloid Formation Independently of the Aggregation Pathway"; Journal of Medicinal Chemistry, vol. 49, No. 20, Oct. 2006, pp. 6057-6064, XP002611490.
Y. Iwamaru et al, "Lactoferrin inhibition of prion replication in prion-irrfected cells", Seigaku, Dec. 25, 2007, p. 4P-0951.
International Search Report of PCT/JP2008/003396, mailing date of Dec. 22, 2008.
Notification of Transmittal of Translation of the International Preliminary Report on Patentability (Form PCT/IB/338) of International Application No. PCT/JP2008/003396 mailed Jun. 17, 2010 with Forms PCT/IB/373 and PCT/ISA/237.

*Primary Examiner* — Zachariah Lucas
*Assistant Examiner* — Michelle S Horning
(74) *Attorney, Agent, or Firm* — Westerman, Hattori, Daniels & Adrian, LLP

(57) ABSTRACT

Disclosed are: a method for detecting pathogenic isoform of prion protein as distinguished from normal prion protein in a simple manner, rapidly, with a high degree of sensitivity and quantitatively without the need of the enzymatic treatment with protease K; and a reagent for use in the method. Specifically disclosed are: a pathogenic isoform of prion protein binder which comprises lactoferrin; and a method for detecting pathogenic isoform of prion protein by using the pathogenic isoform of prion protein binder.

4 Claims, 2 Drawing Sheets

[Fig. 1]
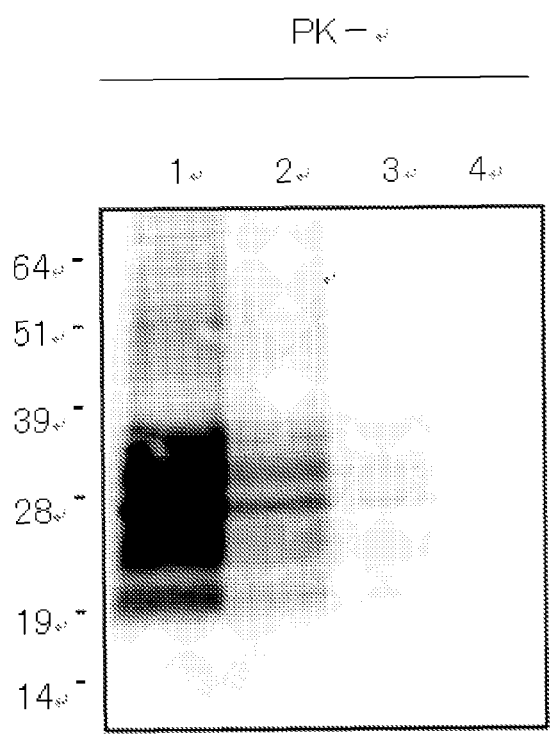
1   Infected brain homogenate (pathogenic isoform of prion protein)
2   Diluted infected brain homogenate (×10)
3   Diluted infected brain homogenate (×100)
4   Noninfected brain homogenate (normal prion protein)

[Fig. 2]
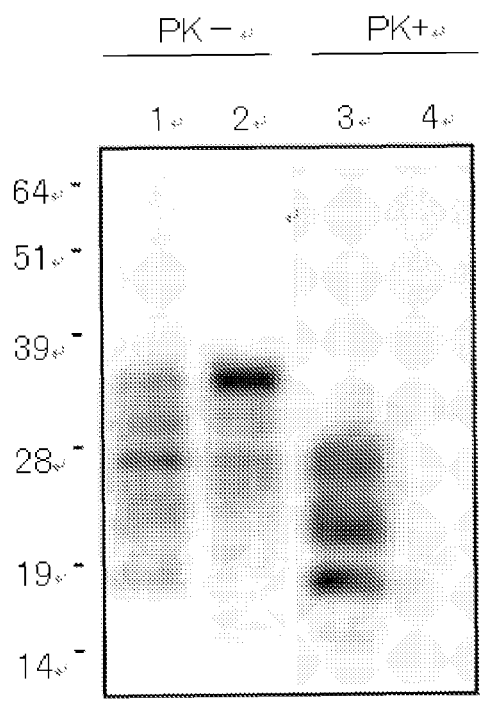
1 Protease K-untreated infected brain homogenate (pathogenic isoform of prion protein)
2 Protease K-untreated noninfected brain homogenate (normal prion protein)
3 Protease K-treated infected brain homogenate (pathogenic isoform of prion protein)
4 Protease K-treated noninfected brain homogenate (normal prion protein)

ABNORMAL PRION PROTEIN BINDER, AND METHOD FOR DETECTION OF ABNORMAL PRION PROTEIN

TECHNICAL FIELD

The present invention relates to a pathogenic (abnormal) isoform of prion protein binder and a method for detecting pathogenic (abnormal) isoform of prion protein.

BACKGROUND ART

So-called "prion diseases" are a serious social problem. Examples of prion diseases include Transmissible Spongiform Encephalopathies (TSEs) such as Scrapie, Bovine Spongiform Encephalopathy (BSE), and Creutzfeldt-Jakob Disease (CJD).

Based on various evidences, it has become clear that such prion diseases are caused by infectious prion protein (pathogenic isoform of prion protein) ($PrP^{sc}$).

In order to prevent transmission of prion diseases of humans and animals and ensure the safety of drugs and foods, various attempts have been made to detect infectious prion protein (pathogenic isoform of prion protein) contained in samples.

However, humans and animals originally have, in their bodies, noninfectious prion protein (normal prion protein) ($PrP^c$) not causing prion diseases. Surprisingly, normal prion protein has the same amino acid sequence (primary structure) as pathogenic isoform of prion protein, and the only difference between normal and pathogenic iso form of prion proteins having the same amino acid sequence is in their higher-order structures.

In general, in a case of detecting two kinds of proteins distinctively from each other, a specific antibody that can distinguish between these two kinds of proteins can be used. However, a specific antibody that can distinguish between pathogenic isoform of prion protein and normal prion protein has not yet been obtained probably due to their identical amino acid sequence described above. That is, there is still no possibility of practical use of a method for detecting infectious prion protein (pathogenic isoform of prion protein) contained in a sample using a specific antibody.

Under the circumstances, a method for detecting pathogenic isoform of prion protein is limited mainly to the following two types.

One is a method in which a sample suspected to contain pathogenic isoform of prion protein (infectious prion protein) is injected into the brains of test animals and the test animals are bred over a long period of time to monitor neuropathological changes in brain specimens from the test animals.

This method is reliable, but unfortunately, requires too much time and money. Therefore, this method is used only to calibrate other various detection methods, and has not reached routine use.

The other one is a method using protease K. It is known that normal prion protein is easily degraded by (i.e., sensitive to) protease K, but on the other hand, pathogenic isoform of prion protein is hard to be degraded by (i.e., resistant to) protease K probably due to their higher-order structures. Therefore, pathogenic isoform of prion protein can be detected by utilizing a difference in sensitivity (resistance) to degradation by protease K between normal and pathogenic isoform of prion proteins. For example, a sample is treated and not treated with protease K, and is then analyzed by, for example, immunoblotting using a polyclonal antibody. In a case where protein bands are detected by immunoblotting of the sample treated with protease K at the same positions as those detected by immunoblotting of the sample not treated with protease K, it is judged that the protein bands represent pathogenic isoform of prion protein. On the other hand, in a case where protein bands detected by immunoblotting of the sample not treated with protease K disappear (i.e., not detected) by immunoblotting of the sample treated with protease K, it is judged that the protein bands represent normal prion protein.

This detection method using protease K is now widely used, and many variations thereof have been proposed (see, for example, Patent Documents 1 to 3).

However, this method necessarily involves enzymatic treatment, and therefore requires time to perform the enzymatic reaction and is complicated in that it is necessary to create conditions suitable for the enzymatic reaction. Therefore, in principle, this method has drawbacks in that it is poor in quickness and simplicity and that a relatively expensive enzyme is absolutely necessary as a reagent.

Patent Document 1: Japanese Patent Application Laid-open No. 10-267928
Patent Document 2: Japanese Patent Application Laid-open No. 11-32795
Patent Document 3: Japanese Patent Application Laid-open No. 2003-121448

DISCLOSURE OF THE INVENTION

Problems to be Solved by the Invention

Under the circumstances, there has been a demand for a method for detecting pathogenic isoform of prion protein distinctively from normal prion protein simply, quickly, and quantitatively with high sensitivity without performing enzymatic treatment using protease K.

It is therefore an object of the present invention to provide a method for detecting pathogenic isoform of prion protein distinctively from normal prion protein simply, quickly, and quantitatively with high sensitivity without performing enzymatic treatment using protease K and a detection agent for use in this method.

Further, there has also been a demand for a reagent (binder) that does not bind to normal prion protein but specifically binds to pathogenic isoform of prion protein for use in such a detection method.

It is therefore another object of the present invention to provide a reagent (binder) that does not bind to normal prion protein but specifically binds to pathogenic isoform of prion protein.

Means for Solving the Problems

In order to achieve the above objects, the present inventors have extensively studied a method for specifically detecting pathogenic isoform of prion protein, and as a result have found that lactoferrin, which is a protein derived from mammalian milk, does not bind to normal prion protein but specifically binds only to pathogenic isoform of prion protein. This finding has led to the completion of the present invention.

That is, lactoferrin is a long-awaited reagent (i.e. a binder, a binding agent, a binder agent) that does not bind to normal prion protein but specifically binds to pathogenic isoform of prion protein. The use of lactoferrin makes it possible to detect pathogenic isoform of prion protein distinctively from normal prion protein without performing enzymatic treatment using protease K.

Further, the utilization of the property of lactoferrin to specifically bind to pathogenic isoform of prion protein makes it possible not only to specifically detect pathogenic isoform of prion protein but also to perform specific separation (including isolation, purification and concentration) of pathogenic isoform of prion protein, specific immobilization of pathogenic isoform of prion protein, and specific inhibition of self-association of pathogenic isoform of prion protein, thereby making it possible to provide new applications that are not possible with a conventional method involving enzymatic treatment with protease K. That is, the pathogenic isoform of prion protein binder according to the present invention has such useful applications.

Accordingly, the present invention provides the following.

(1) A pathogenic isoform of prion protein binder (binding agent) comprising lactoferrin.

(2) A pathogenic isoform of prion protein binder (binding agent) having a pathogenic isoform of prion protein-binding moiety consisting of lactoferrin.

Further, the lactoferrin may be immobilized onto a coupling material (i.e. a carrier, a substrate, a carrier material, a base material). By using such a lactoferrin-immobilized coupling material, it is possible to particularly effectively perform separation of pathogenic isoform of prion protein from normal prion protein (including isolation, purification and concentration of pathogenic isoform of prion protein) to obtain only pathogenic isoform of prion protein, binding and immobilization of pathogenic isoform of prion protein to lactoferrin, and detection of pathogenic isoform of prion protein.

Accordingly, the present invention also provides the following.

(3) The pathogenic isoform of prion protein binder according to the above (1) or (2), wherein the lactoferrin is immobilized onto a coupling material (a carrier).

(4) The pathogenic isoform of prion protein binder according to the above (1) or (2), wherein the lactoferrin is immobilized as a pathogenic isoform of prion protein-binding moiety onto a coupling material (a carrier).

(5) The pathogenic isoform of prion protein binder according to the above (3) or (4), wherein the coupling material is a bead.

(6) The pathogenic isoform of prion protein binder according to the above (5), wherein the bead is a magnetizable bead.

Such a pathogenic isoform of prion protein binder can be used for detecting pathogenic isoform of prion protein.

Accordingly, the present invention also provides the following.

(7) The pathogenic isoform of prion protein binder according to any one of the above (1) to (6), which is a pathogenic isoform of prion protein detection agent.

(8) The pathogenic isoform of prion protein binder according to any one of the above (1) to (6), which is a pathogenic isoform of prion protein detection agent having a pathogenic isoform of prion protein-binding moiety consisting of lactoferrin.

(9) The pathogenic isoform of prion protein binder according to any one of the above (1) to (6), which is a pathogenic isoform of prion protein detection agent having a pathogenic isoform of prion protein-binding moiety constituted of lactoferrin and a labeled moiety.

The present invention is also directed to a pathogenic isoform of prion protein detection method, a pathogenic isoform of prion protein binding method, a pathogenic isoform of prion protein isolation method (including a pathogenic isoform of prion protein purification method, a pathogenic isoform of prion protein separation method and a pathogenic isoform of prion protein concentration method), a pathogenic isoform of prion protein immobilization method, or a method for inhibiting self-association of pathogenic isoform of prion protein, each of which uses the pathogenic isoform of prion protein binder or the pathogenic isoform of prion protein detection agent.

Accordingly, the present invention also provides the following.

(10) A method for detecting pathogenic isoform of prion protein including the steps of-:

bringing a sample into contact with the pathogenic isoform of prion protein binder according to any one of the above (3) to (6);

separating abound component from the pathogenic isoform of prion protein binder brought into contact with the sample; and detecting pathogenic isoform of prion protein contained in the component separated from the pathogenic isoform of prion protein binder.

(11) The method according to the above (10), wherein at the step of detecting pathogenic isoform of prion protein contained in the component separated from the pathogenic isoform of prion protein binder, detection of the pathogenic isoform of prion protein is performed by an immunoassay.

(12) The method according to the above (11), wherein the immunoassay is a Western-blotting method, an ELISA (enzyme-linked immunosorbent assay) method, or an immunoprecipitation method.

(13) A method for isolating pathogenic isoform of prion protein including the steps of:

bringing a sample into contact with the pathogenic isoform of prion protein binder according to any one of the above (3) to (6); and separating a bound component from the pathogenic isoform of prion protein binder brought into contact with the sample.

(14) The method according to any one of the above (10) to (13), wherein the pathogenic isoform of prion protein binder obtained by immobilizing lactoferrin onto a coupling material is a lactoferrin-immobilized bead.

(15) The method according to any one of the above (10) to (13), wherein the pathogenic isoform of prion protein binder is a lactoferrin-immobilized bead using a magnetizable bead.

(16) The method according to any one of the above (10) to (15), wherein the sample is a liquid sample obtained by homogenizing a mixture of animal tissue and a surfactant.

(17) The method according to the above (16), wherein the animal tissue is one or more of mammalian brain, spinal cord, eye, and small intestine tissues.

(18) The method according to any one of the above (10) to (17), wherein the step of separating a bound component is performed by elution with a solution containing lactoferrin.

Further, the present invention also provides the following.

(19) A method for detecting pathogenic isoform of prion protein including the steps of:

allowing lactoferrin to bind to pathogenic isoform of prion protein; and detecting the lactoferrin bound to the pathogenic isoform of prion protein.

(20) A method for detecting pathogenic isoform of prion protein including the steps of:

allowing lactoferrin having a labeled moiety to bind to pathogenic isoform of prion protein; and detecting the labeled moiety of the lactoferrin bound to the pathogenic isoform of prion protein.

(21) A method for inhibiting self-association of pathogenic isoform of prion protein by allowing lactoferrin to bind to the pathogenic isoform of prion protein.

(22) An inhibitor for inhibiting self-association of pathogenic isoform of prion protein, including lactoferrin.

The present invention also provides the use of lactoferrin, lactoferrin having a labeled moiety, or lactoferrin immobilized onto a coupling material for binding to pathogenic isoform of prion protein.

The present invention also provides the use of lactoferrin, lactoferrin having a labeled moiety, or lactoferrin immobilized onto a coupling material for detecting pathogenic isoform of prion protein.

The present invention also provides the use of lactoferrin, lactoferrin having a labeled moiety, or lactoferrin immobilized onto a coupling material for isolating pathogenic isoform of prion protein.

The present invention also provides the use of lactoferrin, lactoferrin having a labeled moiety, or lactoferrin immobilized onto a coupling material for inhibiting self-association of pathogenic isoform of prion protein.

Effects of the Invention

As has been described above, the present invention discloses, for the first time, that lactoferrin does not bind to normal prion protein but specifically binds only to pathogenic isoform of prion protein. According to the present invention based on this finding, it is possible to detect pathogenic isoform of prion protein distinctively from normal prion protein simply, quickly, and quantitatively with high sensitivity without performing enzymatic treatment using protease K.

That is, according to the present invention, it is possible to distinguish pathogenic isoform of prion protein from normal prion protein without performing enzymatic treatment using protease K. This eliminates the need for performing complicated operations to create conditions suitable for enzymatic reaction and the time required to perform enzymatic reaction. As a result, in principle, the method according to the present invention does not have drawbacks associated with enzymatic treatment using protease K such as poor quickness, poor reproducibility, and absolute necessity of a relatively expensive enzyme as a reagent.

Therefore, according to the present invention, it is possible to inspect foods, drinks, and drugs using animal-derived raw materials for contamination by pathogenic isoform of prion protein (infectious prion protein) more simply, quickly, and quantitatively with higher sensitivity at lower cost than ever before. Further, it is also possible to diagnose prion diseases of humans and animals more simply, quickly, and quantitatively with higher sensitivity at lower cost than ever before. This makes it possible to meet the social demand for infection prevention and early diagnosis of prion diseases of humans and animals.

Further, according to the present invention, it is possible to collect pathogenic isoform of prion protein separately from normal prion protein. This makes it possible to isolate, separate, concentrate, and purify pathogenic isoform of prion protein. Therefore, by combining the foregoing aspects of the present invention, it is possible to more effectively perform the above-described inspection for contamination by pathogenic isoform of prion protein (infectious prion protein) and diagnosis of prion diseases of humans and animals.

BRIEF DESCRIPTION OF THE DRAWINGS

FIG. 1 is a photograph showing the results of immunoblotting demonstrating that pathogenic isoform of prion protein specifically binds to lactoferrin-immobilized beads.

FIG. 2 is a photograph showing the results of immunoblotting demonstrating that a conventional detection method involving enzymatic treatment with protease K can distinguish pathogenic isoform of prion protein from normal prion protein.

BEST MODE FOR CARRYING OUT THE INVENTION

Hereinbelow, preferred embodiments of the present invention will be described in detail. However, the present invention is not limited to the following preferred embodiments, and any changes may be made within the scope of the present invention. It is to be noted that in this specification, "percent (%)" refers to "percent (%) by mass" unless otherwise specified.

A preferred embodiment of a method for detecting pathogenic isoform of prion protein according to the present invention includes the steps of: bringing a sample into contact with a pathogenic isoform of prion protein binder obtained by immobilizing lactoferrin onto a coupling material; separating a bound component from the pathogenic isoform of prion protein binder brought into contact with the sample; and detecting pathogenic isoform of prion protein contained in the component separated from the pathogenic isoform of prion protein binder.

According to this detection method, pathogenic isoform of prion protein contained in a sample can be collected by allowing the pathogenic isoform of prion protein to specifically bind (adsorb) to lactoferrin immobilized in a pathogenic isoform of prion protein binder and then separating the pathogenic isoform of prion protein bound to the lactoferrin immobilized in the pathogenic isoform of prion protein binder, and therefore can be detected distinctively from normal prion protein by detecting the pathogenic isoform of prion protein separated from the pathogenic isoform of prion protein binder.

At the step of detecting pathogenic isoform of prion protein contained in the component separated from the pathogenic isoform of prion protein binder, detection of the pathogenic isoform of prion protein is preferably performed by an immunoassay.

Preferred examples of such an immunoassay include a Western-blotting method, an ELISA method, and an immunoprecipitation method.

A method for use in detecting pathogenic isoform of prion protein at the step of detecting pathogenic isoform of prion protein contained in the component separated from the pathogenic isoform of prion protein binder, including the above-mentioned immunoassay, is not particularly limited as long as it can detect pathogenic isoform of prion protein, and therefore a method that cannot distinguish between pathogenic isoform of prion protein and normal prion protein can be of course used. This is because, according to the present invention, specificity for pathogenic isoform of prion protein is previously ensured by allowing pathogenic isoform of prion protein to bind to lactoferrin before the step of detecting pathogenic isoform of prion protein. Therefore, the above-mentioned immunoassay can, of course, use an antibody that does not distinguish between pathogenic isoform of prion protein and normal prion protein.

Lactoferrin (hereinafter, sometimes abbreviated as "LF") is an iron-binding glycoprotein with a molecular weight of about 80 kDa mainly present in breast milk, and is known as a milk protein having various activities such as antibacterial activity against harmful bacteria such as *Escherichia coli, Candida, Clostridium*, and *Staphylococcus*, immuno-modulatory activity, and antitumor activity. As described above, lactoferrin is a milk-derived glycoprotein, and is therefore highly safe and can be continuously taken for a long period of time. Further, lactoferrin itself has almost no taste and odor, and is therefore widely used as an additive for various foods, drugs, and livestock foods. However, the ability of lactoferrin to specifically bind to pathogenic isoform of prion protein has not been previously known.

Lactoferrin to be used in the present invention may be commercially-available one or may be obtained by isolating from a raw material, such as colostrum, milk (transitional milk, mature milk, or late lactation milk) of mammals (e.g., human, bovine, goat, sheep, and horse) or a product obtained by processing such milk such as skimmed milk or whey, by a conventional technique such as ion-exchange chromatography. Particularly, commercially-available lactoferrin produced in an industrial scale (e.g., lactoferrin produced by Morinaga Milk Industry Co., Ltd.) is preferably used. Alternatively, lactoferrins produced using microorganisms, animal cells, transgenic animals or the like by genetic engineering techniques may also be used. As a raw material of lactoferrin to be used in the present invention, whey derived from bovine milk is particularly preferred because it can be stably obtained in large amounts as a by-product of the manufacture of milk products.

Hereinbelow, one example of a method for preparing lactoferrin (isolation of lactoferrin from a raw material such as milk and purification thereof) will be described. First, an ion exchanger (e.g., CM-SEPHAROSE FF manufactured by Amersham Pharmacia) is packed in a column, hydrochloric acid is passed through the column, and the column is washed with water to equilibrate the ion exchanger. Then, skimmed milk with a pH of 6.9 cooled to 4° C. is passed through the column, effluent from the column is recovered, and the effluent is again passed through the column in the same manner. Then, distilled water is passed through the column, and then a salt solution is passed through the column to obtain an eluate containing basic protein adsorbed to the ion exchanger. Then, 80% saturated ammonium sulfate is added to the eluate to precipitate the protein, and then the eluate is centrifuged to obtain a precipitate. The obtained precipitate is washed with an 80% saturated ammonium sulfate solution, and then deionized water is added to the washed precipitate to obtain a solution. Then, the solution is desalted using an ultrafiltration membrane module (e.g., SLP0053 manufactured by Asahi kasei Corporation), and is then freeze-dried to obtain powdered bovine lactoferrin. In this way, bovine lactoferrin with a purity of 95% by mass or higher can be obtained. It is to be noted that in this specification, the purity of lactoferrin is a value measured by liquid chromatography.

Like many proteins, lactoferrin also generally contains a mutation such as substitution, deletion, insertion, addition, or inversion of one or more bases at one or more positions due to a difference in species or genus or a difference between individuals, and amino acids of a protein encoded by a gene having such a mutation may also have a mutation. In the present invention, lactoferrin having such a mutation can also be used as long as its ability to specifically bind to pathogenic isoform of prion protein is not impaired.

Immobilization of lactoferrin onto a coupling material to prepare a pathogenic isoform of prion protein binder can be performed by an immobilization method usually used as long as the ability of lactoferrin to specifically bind to pathogenic isoform of prion protein is not impaired. Examples of such an immobilization method include a method in which a covalent bond is directly formed with a primary amino group of a polypeptide and a method in which a covalent bond is directly formed with a sulfhydryl group (thiol group) of a polypeptide.

A coupling material (i.e. a carrier, a substrate, a carrier material, a base material) used for immobilizing lactoferrin to prepare a pathogenic isoform of prion protein binder is not particularly limited as long as it is a coupling material that is generally used and can function as a solid phase under desired conditions and immobilize a protein. Examples of such a coupling material include ones having a hydrophilic or hydrophobic resin on the surface thereof, and such a coupling material can be formed into various shapes such as particles (beads), films, fibers, hollow fibers, and meshes. Among them, bead-shaped (particulate) coupling materials are preferred. The particle size (diameter) of a bead (particle) can be appropriately selected according to the purpose of use, but is, for example, generally 0.5 to 200 μm, preferably 1.0 to 100 μm, more preferably 1.0 to 50 μm, even more preferably 1.0 to 20 μm, even more preferably 1.0 to 10 μm, particularly preferably 1.0 to 5.0 μm.

As described above, a bead (particle) having a hydrophobic or hydrophilic resin on the surface thereof is preferably used as a coupling material (i.e. a carrier, a substrate, a carrier material, a base material). In this case, a pathogenic isoform of prion protein-binding active coupling material obtained by immobilizing lactoferrin onto a coupling material refers to a lactoferrin-immobilized bead. These beads used as a coupling material can be suspended and dispersed in a liquid, and if operationally necessary, they can be easily precipitated and collected.

More preferably, a bead (particle) having a hydrophobic or hydrophilic resin on the surface thereof and a magnetizable material in the inside (at the center) thereof is used as a coupling material. In this case, a pathogenic isoform of prion protein-binding active coupling material obtained by immobilizing lactoferrin onto a coupling material refers to a lactoferrin-immobilized bead using a magnetizable bead. These beads used as a coupling material can be suspended and dispersed in a liquid, and if operationally necessary, they can be easily precipitated and collected by using a magnet. If operationally necessary, such operation can be performed by those skilled in the art during, before, or after the step of bringing a sample into contact with the lactoferrin-immobilized beads or the step of separating a component bound to the lactoferrin-immobilized beads.

A sample is not particularly limited as long as it is a liquid sample suspected to contain pathogenic isoform of prion protein (infectious prion protein). However, it is preferred that when a sample contains pathogenic isoform of prion protein, the pathogenic isoform of prion protein is sufficiently dispersed in the sample. In a case where a test object is animal tissue, a sample is preferably prepared by sufficiently solubilizing the animal tissue. An example of such a solubilized sample includes a liquid sample obtained by homogenizing a mixture of animal tissue and a surfactant. The pH of such a liquid sample is not particularly limited, but is preferably near neutral. More specifically, the pH is generally 5.5 to 7.8, preferably 6.0 to 7.7, particularly preferably 6.5 to 7.6. The surfactant for use in preparing such a liquid sample is not particularly limited as long as it is a surfactant generally used to solubilize animal tissue, but is preferably a nonionic surfactant from the viewpoints of solubilizing animal tissue and maintaining the higher-order structure of prion protein. Preferred examples of the surfactant include TWEEN 20, TRITON X-100, and NP-40. Among these surfactants, TWEEN 20, TRITON X-100, and NP-40 are preferred, and TWEEN 20 and NP-40 are particularly preferred. From the viewpoint of ensuring specific binding between lactoferrin and pathogenic isoform of prion protein, a sample is preferably prepared as a liquid sample that can be brought into contact with the pathogenic isoform of prion protein-binding active coupling material under the following conditions.

From the viewpoint of ensuring specific binding between lactoferrin and pathogenic isoform of prion protein, a sample is preferably brought into contact with the pathogenic isoform of prion protein-binding active coupling material at a pH of generally 5.5 to 7.8, preferably 6.0 to 7.7, particularly preferably 6.5 to 7.6 at a temperature of generally 3 to 30° C., preferably 3 to 20° C., particularly preferably 3 to 5° C. for generally 5 to 300 minutes, preferably 10 to 180 minutes, particularly preferably 15 to 90 minutes. However, conditions for bringing a sample into contact with the pathogenic isoform of prion protein-binding active coupling material are not limited thereto.

Animal tissue to be solubilized is not particularly limited as long as it is suspected to contain pathogenic isoform of prion protein (infectious prion protein), but from the viewpoint of early diagnosis, one or more of mammalian brain, spinal cord, eye, and small intestine tissues are preferred because it is known that pathogenic isoform of prion protein is mainly present in these tissues.

At the step of separating a bound component from the pathogenic iso form of prion protein binder brought into contact with the sample, the bound component can be separated and eluted by dissociating it from the pathogenic isoform of prion protein binder under relatively strong dissociation conditions among various conditions generally used to dissociate protein-protein interactions. For example, the separation of the bound component can be performed using a surfactant-containing solution at a pH around neutral and a temperature of 3 to 30° C. Alternatively, the separation of the bound component may be performed by dissociating the specific binding between lactoferrin and pathogenic isoform of prion protein by elution using a solution containing lactoferrin.

The preferred embodiment of the pathogenic isoform of prion protein detection method according to the present invention may further include, after the step of bringing a sample into contact with a pathogenic isoform of prion protein binder obtained by immobilizing lactoferrin onto a coupling material but before the step of separating a bound component from the pathogenic isoform of prion protein binder brought into contact with the sample, the step of washing the pathogenic isoform of prion protein binder brought into contact with the sample. The washing step is provided mainly for the purpose of removing a component nonspecifically adsorbed to the pathogenic isoform of prion protein binder brought into contact with the sample when such a component is present. The washing step can be performed by a technique generally used to achieve the purpose described above. Such a technique is not particularly limited, but for example, the washing step can be performed by washing the pathogenic isoform of prion protein binder with a solution which is used for preparing a sample to be brought into contact with the pathogenic isoform of prion protein binder but which contains no solubilized animal tissue or the like.

Further, the present invention also provides a method for isolating pathogenic isoform of prion protein. A preferred embodiment of the method for isolating pathogenic isoform of prion protein according to the present invention includes the steps of: bringing a sample obtained by solubilizing animal tissue into contact with a pathogenic isoform of prion protein binder (binding agent) obtained by immobilizing lactoferrin onto a coupling material (i.e. a carrier, a substrate, a carrier material, a base material); and separating a bound component from the pathogenic isoform of prion protein binder (binding agent) subjected to the step of bringing a sample into contact with a pathogenic isoform of prion protein binder.

According to this isolation method, pathogenic isoform of prion protein contained in a sample can be collected by allowing the pathogenic isoform of prion protein to specifically bind (adsorb) to lactoferrin immobilized in a pathogenic isoform of prion protein binder and then separating the pathogenic isoform of prion protein bound to the lactoferrin immobilized in the pathogenic isoform of prion protein binder, thereby making it possible to isolate, separate, concentrate, and purify the pathogenic isoform of prion protein.

As described above, the embodiment of the method for isolating pathogenic isoform of prion protein according to the present invention can be carried out by performing the same steps as the preferred embodiment of the method for detecting pathogenic isoform of prion protein according to the present invention other than the step of detecting pathogenic isoform of prion protein contained in the component separated from the pathogenic isoform of prion protein binder. Therefore, the above description made with reference to the preferred embodiment of the method for detecting pathogenic isoform of prion protein according to the present invention also applies to the embodiment of the method for isolating pathogenic isoform of prion protein according to the present invention.

A pathogenic isoform of prion protein binder including lactoferrin according to the present invention can be used not only in the above embodiments as a pathogenic isoform of prion protein binder obtained by immobilizing lactoferrin onto a coupling material but also in the following embodiments.

That is, a preferred embodiment using the pathogenic isoform of prion protein binder according to the present invention is a method for detecting pathogenic isoform of prion protein including the steps of: allowing lactoferrin to bind to pathogenic isoform of prion protein; and detecting the lactoferrin bound to the pathogenic isoform of prion protein.

According to this pathogenic isoform of prion protein detection method, lactoferrin can be used as a pathogenic isoform of prion protein binder without particular modification. The detection of pathogenic isoform of prion protein can be performed by detecting lactoferrin bound to the pathogenic isoform of prion protein.

The detection of lactoferrin can be performed by any detection method generally used. For example, an immunoassay using an antibody to lactoferrin can be employed.

Further, another preferred embodiment using the pathogenic isoform of prion protein binder according to the present invention is a method for detecting pathogenic isoform of prion protein including the steps of: allowing lactoferrin having a labeled moiety to bind to pathogenic isoform of prion protein; and detecting the labeled moiety of the lactoferrin bound to the pathogenic isoform of prion protein.

According to this pathogenic isoform of prion protein detection method, lactoferrin having a labeled moiety previously attached thereto is used as a pathogenic isoform of prion protein binder. The detection of pathogenic isoform of prion protein can be performed by detecting the labeled moiety attached to the lactoferrin.

A labeled moiety is not particularly limited as long as it is one that is generally used for biopolymers. Examples of such a labeled moiety include a fluorescent marker, a radiation marker, and an enzymatic marker. Examples of the fluorescent marker include ALEXA FLUOR (registered trademark) dyes (manufactured by Becton, Dickinson and Company) and CYDYE (registered trademark) dyes (manufactured by Becton, Dickinson and Company). Among these fluorescent markers, for example, ALEXA FLUOR (registered trademark) 488, ALEXA FLUOR (registered trademark) 647, CY3, CY5.5, AND CY7 are preferably used. Examples of the radiation marker include $^{14}$C-labeled markers and $^{35}$S-labeled markers. Examples of the enzymatic marker include HRP (Horseradish peroxidase) markers and ALP (Alkaline phosphatase) markers.

The present invention also provides a method for inhibiting self-association of pathogenic isoform of prion protein by using the pathogenic isoform of prion protein binder and an inhibitor for inhibiting self-association of pathogenic isoform of prion protein. It is now believed that a plurality of molecules of pathogenic isoform of prion protein are self-associated to form a multimeric complex and that the pathogenicity of prion diseases is enhanced probably due to the self-association of pathogenic isoform of prion protein. The pathogenic isoform of prion protein binder according to the present invention can inhibit the self-association of pathogenic isoform of prion protein by specifically binding to pathogenic isoform of prion protein. It is to be noted that there is no risk that the pathogenic isoform of prion protein binder according to the present invention adversely affects unknown bio-functions expected to be performed by normal prion protein because the pathogenic isoform of prion protein binder according to the present invention does not bind to normal prion protein.

EXAMPLES

Hereinbelow, the present invention will be described in more detail with reference to the following examples, but is not limited thereto.

Example 1

Detection of Pathogenic isoform of Prion Protein from Infected Brain by Use of Lactoferrin-Immobilized Beads The detection of pathogenic isoform of prion protein by lactoferrin-immobilized beads was performed using mouse brain infected with pathogenic isoform of prion protein in the following manner.

Preparation of Lactoferrin-Immobilized Beads 1 mL of DYNABEADS M-280 Tosylactivated was washed with 1 mL of PBS twice, and then a solution obtained by dissolving 1 mg of lactoferrin in 1 mL of 0.1 M boric acid buffer was added to the DYNABEADS to mix them by inversion for 24 hours at 37° C. Then, supernatant was removed and the DYNABEADS were washed with 1 mL of PBS twice. Then, 1 mL of 0.2 M Tris-hydrochloric acid buffer (pH 8.5) containing 0.1% lactoferrin was added to the DYNABEADS to mix them by inversion for 4 hours at 37° C.

Then, supernatant was removed, and the DYNABEADS were washed with 1 mL of PBS containing 0.1% lactoferrin once, and were further washed with PBS containing 0.1% TWEEN 20 once.

Then, supernatant was removed, and the DYNABEADS were washed with 1 mL of PBS containing 0.1% lactoferrin once. Then, supernatant was removed, and the thus obtained lactoferrin-binding DYNABEADS (hereinafter, also referred to as "lactoferrin-binding beads" or "lactoferrin-immobilized beads") were stored in 1 mL of PBS containing 0.1% lactoferrin.

Preparation of Solubilized Brain Tissue Sample (Brain Homogenate)

Brain was harvested from a mouse infected with pathogenic isoform of prion protein. The pathogenic isoform of prion protein-infected mouse brain (hereinafter, simply referred to also as "infected brain") was placed in a BIOMASHER and centrifuged at 10,000 ×g for 2 minutes to obtain a pellet. Then, NP-40 RIPA was added to the pellet to prepare a 10% (w/v) brain homogenate. The brain homogenate was incubated for 15 minutes at 4° C., stirred, and centrifuged at 10,000 ×g for 2 minutes to obtain supernatant. Then, NP-40 RIPA was added to the supernatant to prepare a 2%(w/v) brain homogenate (i.e., a solubilized brain tissue sample). In this way, a homogenate of the infected brain (hereinafter, also referred to as "infected brain homogenate) was obtained.

Isolation of Pathogenic Isoform of Prion Protein by Lactoferrin-Immobilized Beads 20 μL of the lactoferrin-binding DYNABEADS was added to 500 μL of the brain homogenate, and they were mixed by inversion for 1 hour at 4° C. Then, the DYNABEADS were washed with 1 mL of NP-40 RIPA for 10 minutes three times, and were then further washed with 1 mL of NP-40 RIPA overnight.

The washed lactoferrin-binding DYNABEADS were collected, and 20 μL of a neutral buffer (NUPAGE LDS sample buffer (4×) manufactured by Invitrogen) was added thereto. The resulting mixture was heated for 10 minutes at 95° C. to prepare a test sample.

It is to be noted that the DYNABEADS are magnetic, and therefore, if operationally necessary, the DYNABEADS were collected using a magnet during the operation.

Detection by Immunoblotting

Prion protein contained in the prepared test sample was detected by immunoblotting.

More specifically, the test sample was electrophoresed on a NUPAGE gel (at a constant current of 40 mA for 70 minutes), and then proteins in the gel were transferred to a PVDF membrane by a tank blotter (at a constant current of 220 mA for 60 minutes).

After the completion of transfer, the PVDF membrane was blocked by BLOCK ACE (manufactured by Dainippon Pharmaceutical Co., Ltd.) for 30 minutes at 4° C. Then, a solution containing an HRP-conjugated anti-prion protein monoclonal antibody (T2-HRP) diluted 1/5000 with BLOCK ACE containing 0.1% TWEEN 20 was added to the PVDF membrane, and the PVDF membrane was incubated for 1 hour at 4° C.

The PVDF membrane reacted with the antibody was washed with PBS containing 0.1% TWEEN 20 for 10 minutes three times, and was then developed with a chemiluminescence detection reagent to detect chemiluminescence by an image analyzer.

Comparative Example 1

Detection of Pathogenic Isoform of Prion Protein from Noninfected Brain by Use of Lactoferrin-Immobilized Beads The detection of pathogenic isoform of prion protein by lactoferrin-immobilized beads was performed using normal mouse brain (hereinafter, also referred to as "normal brain" or "noninfected brain") in the following manner.

Preparation of Lactoferrin-Immobilized Beads

Lactoferrin-immobilized beads were prepared in the same manner as in Example 1.

Preparation of Solubilized Brain Tissue Sample (Brain Homogenate)

A homogenate of normal brain (hereinafter, also referred to as "normal brain homogenate" or "noninfected brain homogenate") was prepared in the same manner as in Example 1 except that brain harvested from a normal mouse (noninfected mouse) was used instead of the mouse brain infected with pathogenic isoform of prion protein.

Isolation of Pathogenic Isoform of Prion Protein by Lactoferrin-Immobilized Beads A test sample was prepared in the same manner as in Example 1 except that the noninfected brain homogenate was used instead of the infected brain homogenate.

Detection by Immunoblotting

The detection of prion protein was performed in the same manner as in Example 1 except that the test sample derived from the noninfected brain homogenate was used instead of the test sample derived from the infected brain homogenate.

Results

FIG. 1 is a photograph showing the results of immunoblotting performed in Example 1 and Comparative Example 1. All lanes represent samples untreated with protease K (PK−).

Lanes 1, 2, and 3 represent the test sample obtained in Example 1 by performing separation of pathogenic isoform of prion protein by the lactoferrin-immobilized beads on the infected brain homogenate. More specifically, Lane 2 represents the test sample 10 times dilution of that in Lane 1, and Lane 3 represents the test sample 100 times dilution of that in Lane 1. On the other hand, Lane 4 represents the test sample obtained in Comparative Example 1 by performing separation of pathogenic isoform of prion protein by the lactoferrin-immobilizing beads on the noninfected brain homogenate.

In Lanes 1 to 3, prion protein bands were concentration-dependently observed. Even in Lane 3 representing the test sample 100 times dilution of that in Lane 1, prion protein bands were clearly observed. As described above, since the test sample in Lanes 1 to 3 is derived from the infected brain homogenate, the prion protein bands observed in Lanes 1 to 3 are pathogenic isoform of prion protein bands. This indicates that pathogenic isoform of prion protein derived from the infected brain was isolated and detected by binding to the lactoferrin-immobilized beads.

On the other hand, in Lane 4, prion protein bands were not observed in spite of the fact that the concentration of the test sample in Lane 4 was operationally at the same level as that of the test sample in Lane 1. This indicates that normal prion protein derived from the noninfected brain was not bound to the lactoferrin-immobilized beads, and was therefore not collected and detected.

From the results described above, it has been found that pathogenic isoform of prion protein derived from the infected brain specifically binds to the lactoferrin-immobilized beads but normal prion protein derived from the noninfected brain does not bind to the lactoferrin-immobilized beads. Further, it has been also found that pathogenic isoform of prion protein can be collected separately from normal prion protein by using the lactoferrin-immobilized beads, thereby making it possible to detect pathogenic isoform of prion protein.

Comparative Example 2

Detection of Pathogenic Isoform of Prion Protein Using Protease K

An experiment aimed at detecting pathogenic isoform of prion protein distinctively from normal prion protein was performed by a conventional method using protease K as follows.

Preparation of Brain Homogenate

The brain of a pathogenic isoform of prion protein-infected mouse (hereinafter, also referred to as "infected brain") and the brain of a noninfected mouse (normal mouse) (hereinafter, also referred to as "noninfected brain" or "normal brain") were prepared, and each of the mouse brains was placed in a BIOMASHER and centrifuged at 10,000 ×g for 2 minutes to obtain a pellet. Then, NP-40 RIPA was added to the pellet to prepare a 10% (w/v) brain homogenate. The brain homogenate was incubated for 15 minutes at 4° C., stirred, and centrifuged at 10,000 ×g for 2 minutes to obtain supernatant. Then, NP-40 RIPA was added to the supernatant to prepare a 0.5% (w/v) brain homogenate. In this way, an infected brain homogenate and a noninfected brain homogenate were obtained.

Enzymatic Degradation by Protease K

Proteinase K was added to 500 μL of each of the brain homogenates so that the final concentration of the proteinase K was 20 μg/mL, and then the resulting mixture was incubated for 30 minutes at 37° C. After the completion of reaction, 5 μL of a proteinase K inhibitor (Pefablock) and then 250 μL of a Buthanol-Methanol solution were added thereto, stirred, and centrifuged at 20,000 ×g for 10 minutes to obtain a pellet. After the completion of centrifugation, 50 μL of a neutral buffer (NUPAGE LDS sample buffer (4×), manufactured by Invitrogen) was added to the pellet, and the resulting mixture was heated for 10 minutes at 95° C. In this way, a sample derived from the infected brain homogenate and a sample derived from the noninfected brain homogenate were obtained.

Detection by Immunoblotting

The detection of prion protein was performed by immunoblotting on the thus obtained four kinds of samples, i.e., on the infected brain homogenate subjected to enzymatic degradation by protease K (protease K-treated infected brain homogenate), the noninfected brain homogenate subjected to enzymatic degradation by protease K (protease K-treated noninfected brain homogenate), the infected brain homogenate not subjected to enzymatic degradation by protease K (original infected brain homogenate), and the noninfected brain homogenate not subjected to enzymatic degradation by protease K (original noninfected brain homogenate).

More specifically, the samples were electrophoresed on a NUPAGE gel (at a constant current of 40 mA for 70 minutes), and then proteins in the gel were transferred to a PVDF membrane using a tank blotter (at a constant current of 220 mA for 60 minutes).

After the completion of transfer, the PVDF membrane was blocked using BLOCK ACE (manufactured by Dainippon Pharmaceutical Co., Ltd.) for 30 minutes at 4° C. Then, a solution containing an HRP-conjugated anti-prion protein monoclonal antibody (T2-HRP) diluted 1/5000 with BLOCK ACE containing 0.1% TWEEN 20 was added to the PVDF membrane, and the PVDF membrane was incubated for 1 hour at 4° C.

The PVDF membrane reacted with the antibody was washed with PBS containing 0.1% TWEEN 20 for 10 minutes three times and developed with a chemiluminescence detection reagent to detect chemiluminescence by an image analyzer.

Results

FIG. 2 is a photograph showing the results of immunoblotting performed in Comparative Example 2. Lanes 1 and 2 represent samples not subjected to enzymatic degradation by protease K (PK−), and Lanes 3 and 4 represent samples subjected to enzymatic degradation by protease K (PK+).

More specifically, Lane 1 represents the infected brain homogenate not subjected to enzymatic degradation by protease K (i.e., the original infected brain homogenate), and Lane 2 represents the noninfected brain homogenate not subjected to enzymatic degradation by protease K (i.e., the original noninfected brain homogenate). On the other hand, Lane 3 represents the infected brain homogenate subjected to enzymatic degradation by protease K (i.e., the protease K-treated infected brain homogenate), and Lane 4 represents the noninfected brain homogenate subjected to enzymatic degradation by protease K (i.e., the protease K-treated noninfected brain homogenate).

As shown in FIG. 2, in both Lanes 1 and 2, prion protein bands were detected by immunoblotting. This indicates that when enzymatic treatment with protease K is not performed, both pathogenic isoform of prion protein (Lane 1) and normal prion protein (Lane 2) are detected. On the other hand, in Lanes 3 and 4, prion protein bands (pathogenic isoform of prion protein) were detected by immunoblotting only in Lane 3 and no prion protein bands (normal prion protein) were detected in Lane 4. This indicates that enzymatic treatment with protease K makes it possible to distinguish between pathogenic isoform of prion protein and normal prion protein and detect only pathogenic isoform of prion protein.

The results shown in FIG. 2 (Comparative Example 2) were compared with the results shown in FIG. 1 (Example 1 and Comparative Example 1), and as a result, it has been found that the level of accuracy and reliability of the distinction between pathogenic isoform of prion protein and normal prion protein made using the lactoferrin-immobilized beads is the same as or higher than that by a conventional method using protease K.

Industrial Applicability

According to the present invention, it is possible to inspect foods, drinks, and drugs using animal-derived raw materials for contamination by pathogenic isoform of prion protein (infectious prion protein) more simply, quickly, and quantitatively with higher sensitivity at lower cost than ever before. Further, it is also possible to diagnose prion diseases of humans and animals more simply, quickly, and quantitatively with higher sensitivity at lower cost than ever before. This makes it possible to meet the social demand for infection prevention and early diagnosis of prion diseases of humans and animals. As described above, the present invention has industrial applicability.

The invention claimed is:

1. A method for detecting a pathogenic isoform of a prion protein, comprising:
    bringing a sample into contact with lactoferrin;
    separating a bound component from the lactoferrin brought into contact with the sample; and
    detecting a pathogenic isoform of a prion protein contained in the component separated from the lactoferrin.

2. The method according to claim 1, wherein the step of detecting the pathogenic isoform of the prion protein contained in the component separated from the lactoferrin is performed by an immunoassay.

3. A method for isolating a pathogenic isoform of a prion protein, comprising:
    bringing a sample into contact with lactoferrin; and
    separating a bound component from the lactoferrin brought into contact with the sample.

4. The method according to claim 1 or 3, wherein the lactoferrin is immobilized onto a coupling material.

* * * * *